United States Patent [19]

Sugimoto

[11] 4,429,277
[45] Jan. 31, 1984

[54] NUCLEAR MAGNETIC RESONANCE APPARATUS UTILIZING MULTIPLE MAGNETIC FIELDS

[75] Inventor: Hiroshi Sugimoto, Ootawara, Japan

[73] Assignee: Tokyo Shibaura Denki Kabushiki Kaisha, Japan

[21] Appl. No.: 265,643

[22] Filed: May 20, 1981

[30] Foreign Application Priority Data

Jun. 13, 1980 [JP] Japan .................................. 55-79788

[51] Int. Cl.³ .......................................... G01R 33/08
[52] U.S. Cl. ...................................... 324/309; 324/319
[58] Field of Search .............. 324/300, 307, 319, 320, 324/318, 309

[56] References Cited

U.S. PATENT DOCUMENTS

| | | | |
|---|---|---|---|
| 3,234,435 | 2/1966 | Hempstead | 324/319 |
| 3,418,538 | 12/1968 | Roman | 324/319 |
| 3,789,832 | 2/1974 | Damadian . | |
| 3,932,805 | 1/1976 | Abe | 324/309 |
| 4,015,196 | 3/1977 | Moore | 324/309 |
| 4,374,360 | 2/1983 | Sepponen | 324/320 |

OTHER PUBLICATIONS

P. C. Lautebar, "Image Formation by Induced Local Interactions: Examples Employing Nuclear Magnetic Resonance", Nature, vol. 242, 3/16/84-pp. 190–191.
Crooks et al., "Tomographic Imaging with Nuclear Magnetic Resonance", Investigative Radiology, Jan.-Feb. 1978, pp. 63–66.

Primary Examiner—Michael J. Tokar
Attorney, Agent, or Firm—Finnegan, Henderson, Farabow, Garrett & Dunner

[57] ABSTRACT

A nuclear magnetic resonance apparatus for registering the nuclear magnetic resonance condition of atomic nuclei distributed in a body including first magnetic field generating means for generating a homogeneous static magnetic field having a thin beam shape for application to a selected portion of the body, second magnetic field generating means for simultaneously generating a gradient magnetic field of smaller intensity than that of the beam-shaped static magnetic field and of such distribution as to gradually increase or decrease in the direction of the beam-shaped static magnetic field, an oscillator for generating electromagnetic waves having a frequency corresponding to the nuclear magnetic resonance condition of the specific atomic nuclei to be measured, a coil wound around the body to be examined, at least a portion of said coil lying in said magnetic fields, impressing the electromagnetic waves upon the body and for detecting the nuclear magnetic resonance in the body, drive means for moving the body in a direction perpendicular to the beam-shaped magnetic field, a receiver for receiving and processing the nuclear magnetic resonance signal detected by the coil, a recorder for recording the nuclear magnetic resonance signal processed by the receiver in synchronism with the operation of the drive means for identifying the recorded resonance signal with the position of the body, and a display unit for reading the records as to a desired region of the body out of said recorder and for selectively or simultaneously displaying the distribution and relaxation time of the relevant atomic nuclei in the body.

9 Claims, 11 Drawing Figures

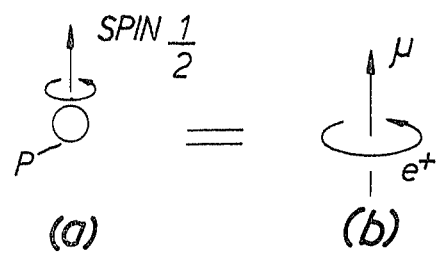
FIG.1.
FIG.2.
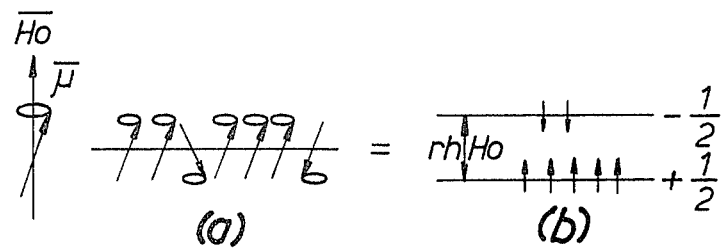
FIG.3.
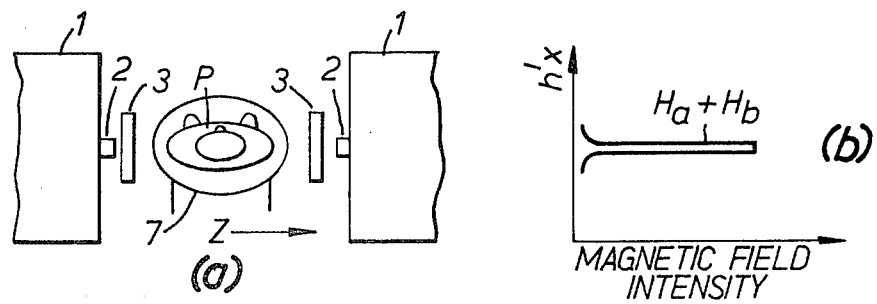
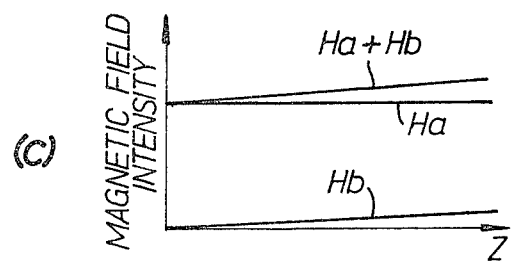
FIG.5.

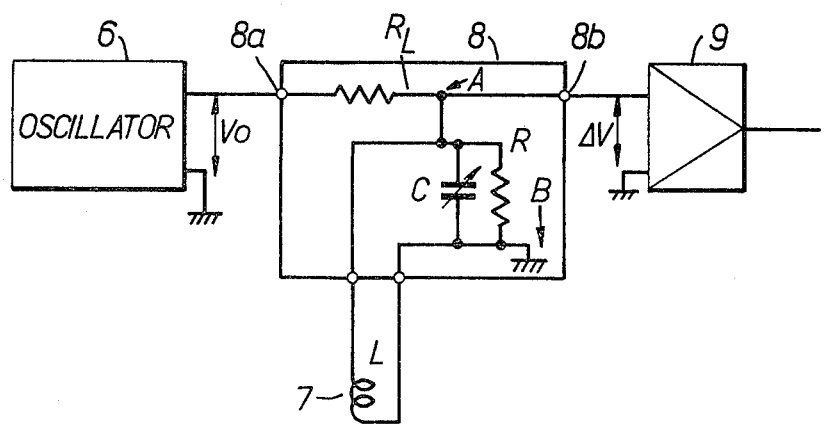
FIG. 7.
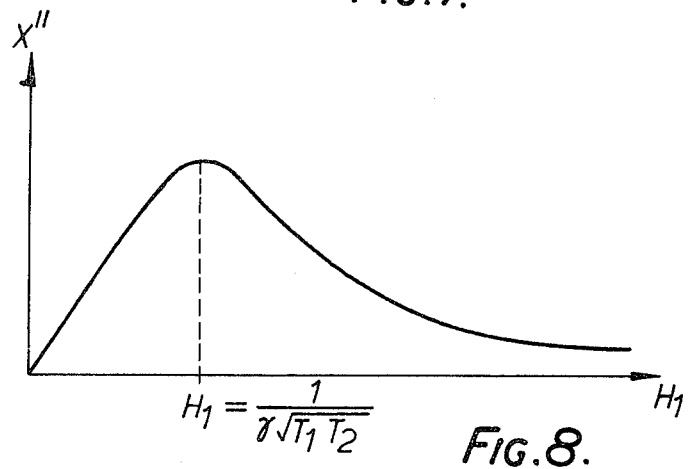
FIG. 8.
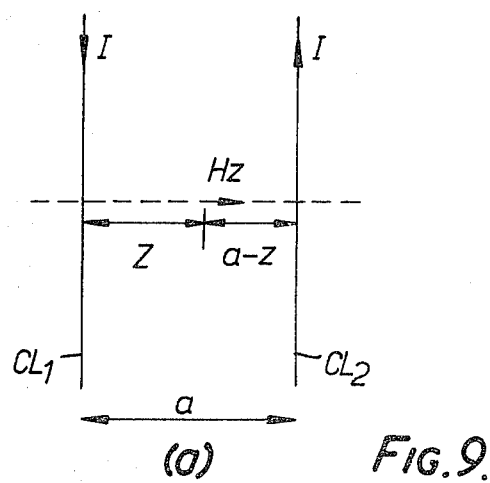
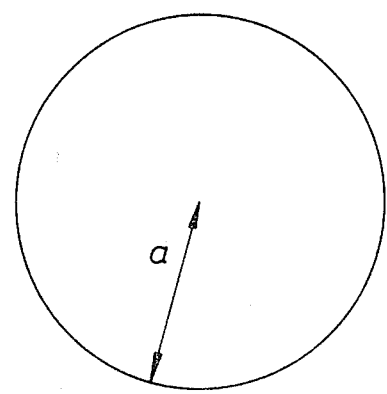
(a) FIG. 9. (b)

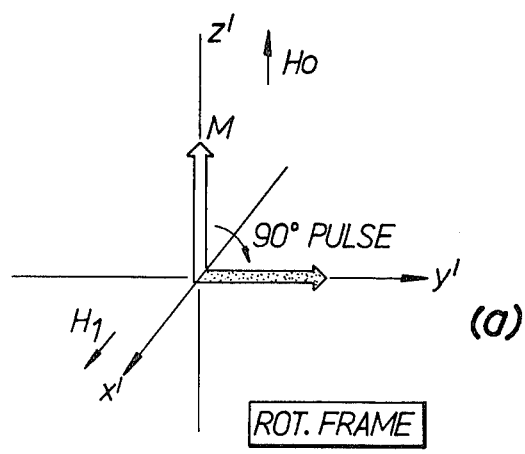
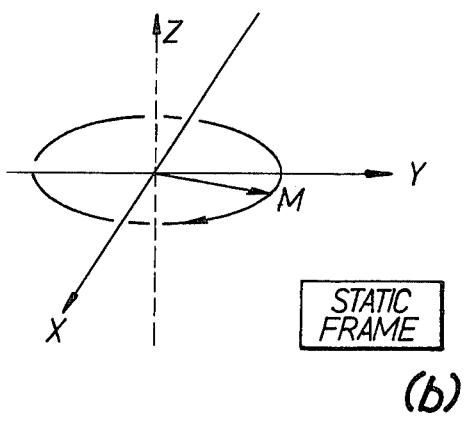
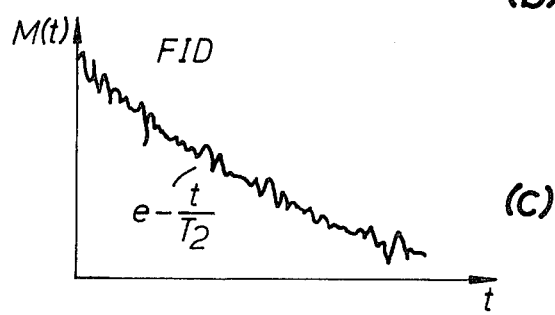
FIG. 10.

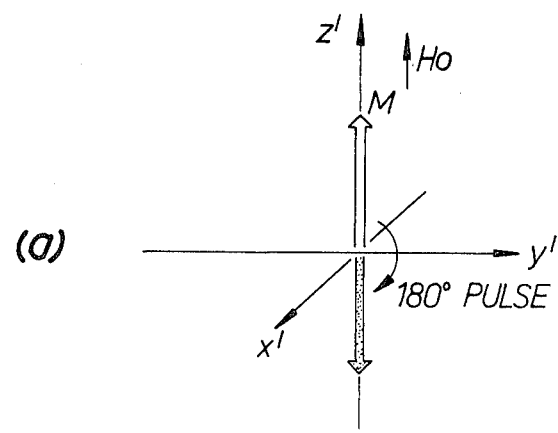
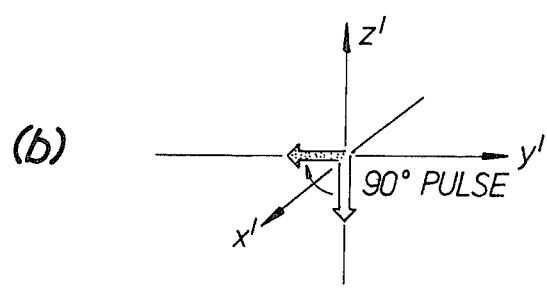
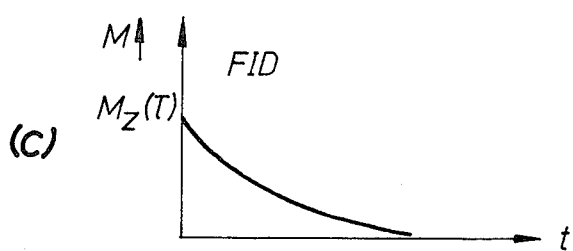
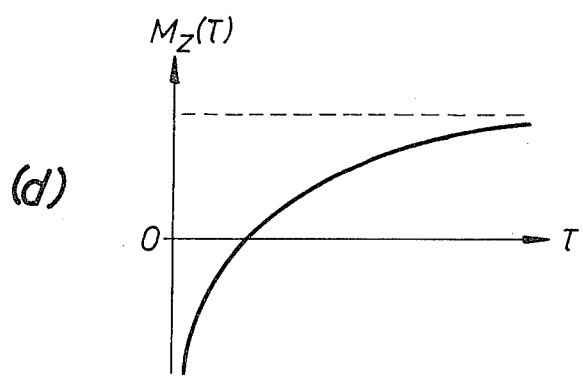
FIG. 11.

NUCLEAR MAGNETIC RESONANCE APPARATUS UTILIZING MULTIPLE MAGNETIC FIELDS

BACKGROUND OF THE INVENTION

This invention relates to a nuclear magnetic resonance apparatus for measuring from outside of a body both the distribution of a specific atomic nucleus in the body to be examined and the relaxation time of the atomic nucleus by making use of the nuclear magnetic resonance (NMR) phenomena.

As an apparatus for examining the internal organs and tissues in a human body from the outside, the following apparatus have been widely used in the prior art:
  X-ray apparatus (including computer tomography apparatus, i.e., a CT scanner);
  nuclear medical apparatus; and
  ultrasonic apparatus.
Each of these apparatus has its respective advantages and disadvantages. For the purposes herein, only the brief descriptions necessary for the comparison with the NMR apparatus according to the invention will be set forth.

The prior art apparatus measure mainly the physical properties of a human body. More specifically, X-ray apparatus discriminates between human tissues and defines their shapes in accordance with the differences in the X-ray transmission characteristics among the human tissues so that a variety of diseases or conditions can be identified. On the other hand, ultrasonic apparatus finds the differences in acoustic impedance among the human tissues thereby to discriminate between tissues and to measure their shapes and motions. However, the nuclear medical apparatus measures the distribution of a radioactive isotope, or its compound, with which a human body has been dosed, and is thereby able to distinguish among the human tissues and to some extent determine the conditions of the respective tissues. Therefore, the nuclear medical apparatus aims mainly at gathering macroscopic information as to each tissue although it can attain biological information to some extent.

Thus, it is difficult for the conventional apparatus in examining a human body from the outside to gather biochemical information concerning the human tissues. More specifically, if the same X-ray transmission characteristic or acoustic impedance is exhibited, it is quite difficult to judge whether that particular tissue is biochemically normal or abnormal (e.g., cancerous). Especially X-ray apparatus has the disadvantage of the exposure of the tissues of the body to X-rays from the outside of the body, and the nuclear medical apparatus has the disadvantage of the exposure of the tissues of the body to $\gamma$-rays from the inside of the body.

As is well-known in the art, for example, examinations are widely performed at present to sample cells and take their photographs by means of a gastro-camera. Some tissues and fluids, such as blood, can also be biochemically analyzed. According to this art, however, the tissues to be examined are restricted, and it is difficult to examine the tissues at the respective portions of a human body from the outside.

By the use of the principle of the NMR, on the contrary, it is possible to attain even biochemical information of the respective tissues in the human body from outside the body.

First of all, the principle of the NMR will be generally explained.

Atomic nuclei are composed of protons and neutrons. In some atomic nuclei, the protons and neutrons spin as a whole like a top, having a nuclear spin angular momentum denominated $\vec{I}$. For example, the atomic nucleus ($^1H$) of hydrogen is composed of a single proton having a spin expressed by a spin quantum number of $\frac{1}{2}$, as shown in FIG. 1(a). Here, since the proton P has a positive electric charge e+, as shown in FIG. 1(b), the phenomenon has the same electrical result as that produced when a current corresponding to the positive charge flows through a small coil in accordance with the spins of the nucleus so that a magnetic momentum $\vec{\mu}$ is established. In other words, each hydrogen nucleus can be deemed as a small magnet.

As is diagrammatically shown in FIGS. 2(a) and 2(b), since a ferromagnetic element such as iron has its minute magnets oriented in the same direction (as shown in FIG. 2(a)), magnetization is observed as a whole. In the case of the aforementioned hydrogen, on the contrary, the directions of the respective magnetic momentums are at random (as shown in FIG. 2(b)) so that magnetization is not observed as a whole.

If a static magnetic field Ho in a direction Z is applied to the hydrogen, the respective atomic nuclei are rearranged in the direction Z of the static magnetic field Ho, i.e., the energy levels of the nuclei are quantized in the direction Z. This phenomena for the hydrogen nucleus is shown in FIG. 3(a). Since the spin quantum number of the hydrogen nucleus is $\frac{1}{2}$, the energy level is divided into two levels, i.e., $-\frac{1}{2}x\Delta E$ and $+\frac{1}{2}x\Delta E$, as shown in FIG. 3(b), but most of the nuclei are oriented in the direction Z corresponding to the energy level of $+\frac{1}{2}x\Delta E$. The energy difference between two energy levels is given by the following equation:

$$\Delta E = \gamma \hbar Ho \qquad (1)$$

wherein:
  $\gamma$: a gyromagnetic ratio; and
  $\hbar$: $h/2\pi$ (h: Planck constant).
If a force defined by $\vec{\mu} \times \vec{Ho}$ is applied to each atomic nucleus by a static magnetic field Ho, the atomic nucleus performs a precession around the axis $\vec{Z}$ at an angular velocity defined by the following equation:

$$\omega = \gamma Ho \text{ (which is called the Lamor angular velocity)} \qquad (2)$$

If electromagnetic waves (which are usually radio-frequency waves) having a frequency corresponding to the angular velocity are applied to the apparatus at that state, resonance takes place so that the atomic nuclei absorb the energy $\gamma \hbar Ho$ corresponding to the aforementioned energy difference $\Delta E$ until they transit to the next higher energy level.

Even if several kinds of atomic nuclei having nuclear spin angular momentums are mixed, the gyromagnetic ratios $\gamma$ are different among the respective atomic nuclei so that the resonance frequencies are accordingly different thereamong. Therefore, the resonance of a specific atomic nucleus can be extracted. Moreover, if the intensity of the resonance is measured, the quantity of the atomic nuclei in the area in question can be obtained. After the resonance, on the other hand, the atomic nucleus, which was excited to a higher energy level, after the time determined by a time constant called a relaxation time has elapsed, returns to its lower energy level. The relaxation time, especially the spin-lattice relaxation time denoted at T1, is a time constant dependent upon the manner of combination of individual chemical compounds and is known to be very different for normal tissues and malignant tissues.

Although the foregoing description has been directed to the atomic nucleus ($^1$H) of hydrogen, other atomic nuclei having different nuclear spin angular momentums can be used to perform similar measurements. For example, in the usual chemical analysis, the atomic nucleus ($^{19}$F) of fluorine, the atomic nucleus ($^{31}$P) of phosphorus, the atomic nucleus ($^{13}$C) of carbon and so on are employed in addition to the aforementioned atomic nucleus ($^1$H) of hydrogen.

Thus, since the quantity of a specific atomic nucleus existing and its relaxation time can be measured by the NMR, chemical information as to a specific atomic nucleus existing in a substance can be obtained.

As an examining apparatus making use of NMR, there has been proposed an apparatus in which an NMR signal corresponding to each projection image of a body to be examined is measured in a number of directions with respect to the body on the basis of a similar principle to the so-called "first generation i.e., translate-rotate type, CT scanner" so that its intensity at each position of the body may be determined by the reconstructing method. ("Image Formation by Induced Local Interactions: Examples Employing Nuclear Magnetic Resonance," by P. C. Lauterbur, "NATURE" vol. 242, Mar. 16, 1973, pp. 190-191).

However, the apparatus proposed has a disadvantage in that it takes a long time to accomplish the measurements. Since it is difficult especially for the NMR to have a signal/noise (S/N) ratio as high as the X-ray, a measurement time larger than one order longer than that of the first generation CT scanner is required for accomplishing measurements which are worthy of examination.

SUMMARY OF THE INVENTION

It is accordingly the object of this invention to provide a nuclear magnetic resonance apparatus which can measure the distribution of a specific atomic nucleus in a body to be examined and its relaxation time on the basis of the NMR principle within a relatively short time period without any reconstructing processing.

Briefly, this and other objects are achieved in accordance with the invention, by constructing a nuclear magnetic resonance apparatus for registering the nuclear magnetic resonance condition of atomic nuclei distributed in a body, the apparatus comprising:

first magnetic field generating means for generating a homogeneous static magnetic field having a thin beam shape for application to a selected portion of the body, second magnetic field generating means for simultaneously generating a gradient magnetic field of smaller intensity than that of the beam-shaped static magnetic field and of such distribution as to gradually increase or decrease in the direction of said beam-shaped static magnetic field, an oscillator for generating electromagnetic waves having a frequency corresponding to the nuclear magnetic resonance condition of the atomic nuclei to be measured, a coil wound around the body to be examined, at least a portion of the coil lying in said beam-shaped static magnetic field for impressing the electromagnetic waves upon the body and for detecting the nuclear magnetic resonance in the body, drive means for moving said body in a direction perpendicular to the beam-shaped magnetic field, a receiver for receiving and processing the nuclear magnetic resonance signal detected by the coil, a recorder for recording the nuclear magnetic resonance signal processed by said receiver in synchronism with the operation of the drive means for identifying the recorded resonance signal with the position of the body, and a display unit for reading the records as to a desired region of the body out of the recorder and to selectively or simultaneously display the distribution and relaxation time of the relevant atomic nuclei in the body.

BRIEF DESCRIPTION OF THE DRAWINGS

FIGS. 1(a) and 1(b) are schematic views for explaining nuclear magnetic momentum;

FIGS. 2(a) and 2(b) are schematic views for explaining the arrangement of nuclear magnetic momentum;

FIGS. 3(a) and 3(b) are schematic views for explaining the alignment of the nuclear magnetic momentum by a static magnetic field;

FIGS. 5(a) to 5(c), FIG. 6 and FIG. 8 are views and graphs for explaining the embodiment of FIG. 4;

FIG. 7 is a circuit diagram showing in detail a portion of the construction of the embodiment of FIG. 4;

FIGS. 9(a) and 9(b) are schematic views for explaining the Helmholtz coil as an example of means for generating a gradient magnetic field; and FIGS. 10(a) to 10(d) and FIGS. 11(a) to (d) are schematic views for explaining other embodiments of the invention.

DESCRIPTION OF THE PREFERRED EMBODIMENTS

Figure 4:
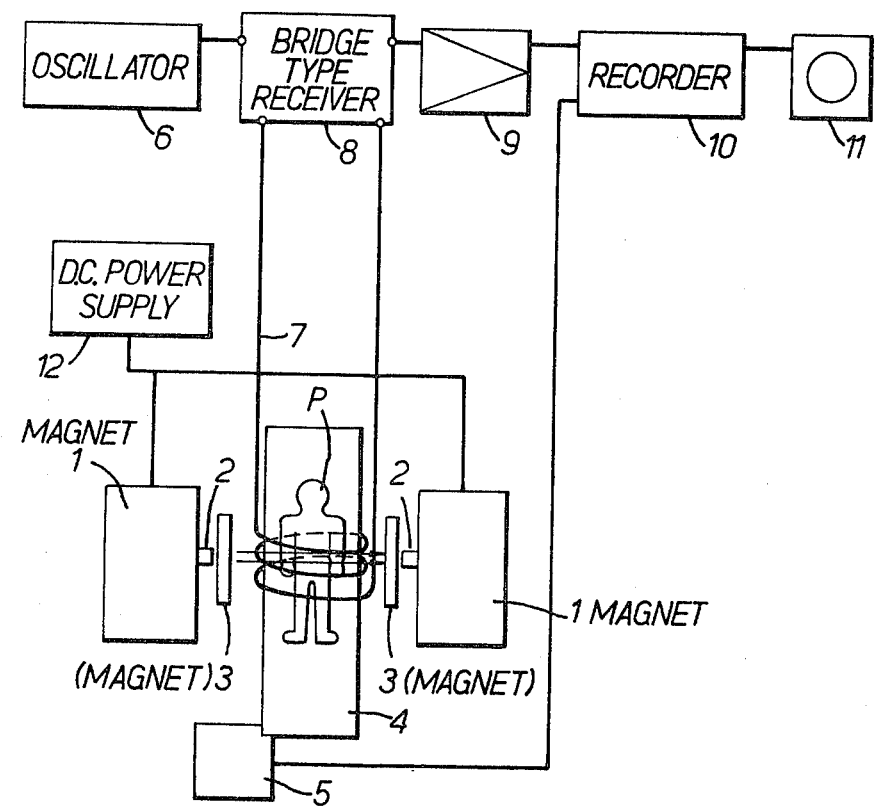
FIG. 4 is a block diagram showing the construction of one embodiment of this invention.

Referring to FIG. 4, first magnet means 1 is composed of a pair of magnets, such as electromagnets driven by a D.C. stabilized power supply 12, to generate a homogeneous static magnetic field. Shims (or pole pieces) 2 of a magnetic substance are magnetically and slidably mounted to protrude from the facing magnetic pole plates of the pair of first magnet means for focusing the homogeneous static magnetic field generated by the first magnet means into a thin beam (or the so-called "pencil beam") shape.

Second magnet means 3 is composed of a pair of magnets such as a Helmholtz coil driven by a stabilized power supply for generating, in addition to the beam-shaped magnetic field focused by the shims 2, a gradient magnetic field having such an intensity as is distributed to gradually increase or decrease in the direction of the beam.

A body holder 4, such as a bed structure, holds a body P to be examined. Drive means 5 may drive the body holder 4 so as to drive the body P in either of two directions perpendicular to the aforementioned beam and to each other as required to expose the portion of the body under examination to the magnetic fields and the electromagnetic waves.

An oscillator 6 generates a signal having a frequency corresponding to the NMR condition of an atomic nucleus to be measured. A coil 7 is wound around the body P for applying the signal generated by the oscillator 6 in the form of electromagnetic waves to the body P and for detecting the NMR at the body P. A so-called "bridge-type receiver" 8 transmits the output signal of the oscillator 6 to the coil 7 and receives the NMR signal from the coil 7. A phase-sensitive AM amplifier 9 detects and amplifies the NMR signal received and detected by the receiver 8.

A recorder 10 records the output of the amplifier 9 in a manner to correspond to the position in the body P with reference to the drive signals of the drive means 5. A display unit 11 reads the record out of the recorder 10 and displays the record for read out.

In this instance, the first magnet means 1 and the shims 2 constitute first magnetic field generating means for generating a homogeneous static magnetic field having a thin beam shape, whereas the second magnet means 3 constitutes the second magnetic field generating means for generating a gradient magnetic field.

With the construction thus far described, the body P is irradiated with a focused thin magnetic field Ha, as shown in FIGS. 5(a) to (c), which is focused from a homogeneous static magnetic field Ho by the actions of both the first magnet means 1 for generating the homogeneous static magnetic field Ho and the shims 2 disposed to protrude from the facing magnetic pole plates of the first magnet means 1 for focusing the magnetic field into the thin beam shape. The other magnetic field, with which the body is irradiated by the second magnet means generating the gradient magnetic field, has an intensity as of about 1/100 or less than the homogeneous static magnetic field Ho and has a gradually differing intensity (in the direction Z) within the body P.

In addition, high-frequency waves generated by the oscillator 6, which is operative to oscillate in a frequency within the band of the resonance frequency $\omega$, are applied as electromagnetic waves to the body P through the coil 7 wound around the body P.

Simultaneously, a resonance signal is extracted by the bridge-type receiver 8 to generate an output corresponding to the change in the resonance of the received signal from the input signal from the oscillator 6. After this output has been amplified by the amplifier 9, the resonance intensity is fed to the recorder 10. This recorder 10 is also fed with a moving position signal from the driving means 5, which is operative to mechanically move the body holder 4, so that it may record the intensity of the resonance signal in a manner to correspond to the respective positions of the body P. The results are displayed in the display unit 11 so that they may be used visually for the examination.

Figure 6:
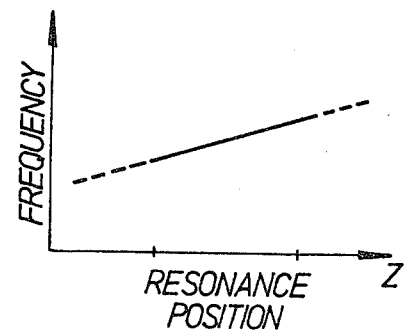

More specifically, the body P has a portion exposed to a magnetic field which is the summation of the beam-shaped homogeneous static magnetic field Ha and the gradient magnetic field Hb. The overall magnetic field (Ha+Hb) is very narrow in the X, Y plane and, as shown in FIG. 5(b), and is gradient in the direction Z, as shown in FIG. 5(c). As has been described before, since there holds between the intensity H of the magnetic field and the resonance frequency $\omega$ the following relationship:

$$\omega = \gamma H \tag{2}$$

the resonance frequency becomes gradually different at the respective positions in the body P in the direction Z due to the influence of the gradient magnetic field, as shown in FIG. 6.

If the resonance signal is taken at different successive frequencies generated by the oscillator 6, the result is that a beam-shaped slender column region is scanned. The range to be scanned can be suitably selected by selecting the frequency range to be generated. By repeating similar scanning operations at different positions of the body P, the NMR resonance signal at any region can be extracted from not only the transverse section of the body P but also from the flat or curved plane in any direction.

The bridge type receiver 8 is constructed as shown in FIG. 7. A resistor $R_L$ is connected between an input terminal 8a, to which the oscillator 6 is connected, and an output terminal 8b which is connected to the amplifier 9. A parallel circuit, including a variable capacitor C and resistor $R_B$, is connected across the terminals of the coil 7. One common terminal A of the coil 7 and the parallel circuit is connected between the resistor $R_L$ and the output terminal 8b and the other common terminal B is grounded. If the variable capacitor C is adjusted for the inductance L of the coil as determined by the following equation:

$$\omega = 1/\sqrt{LC}, \tag{3}$$

the impedance $Z_{AB}$ between points A and B is given for the susceptibility X of the exposed portion of the body P by the following equation:

$$Z_{AB} = R\left(1 - 4\pi i X \frac{R}{\omega L}\right) \tag{4}$$

wherein i is $\sqrt{-1}$. (As used herein, "susceptibility" means the impedance due to the change in energy level of the atomic nuclei under the force of the magnetic fields and/or the electromagnetic waves.) Consequently, the received voltage V between the points A and B is given by the following equation:

$$V = Vo\left(1 - 4\pi i X \frac{R}{\omega L}\right). \tag{5}$$

Of the voltage V detected (simultaneously as it is amplified by the AM detecting amplifier 9), the imaginary part X" of the susceptibility X is defined by the following equation:

$$|V| = |Vo|\left(1 - 4\pi X'' \frac{R}{\omega L}\right). \tag{6}$$

so that the voltage difference defined by the following equation becomes the output signal:

$$\Delta V = |V| - |Vo| \tag{7}$$

$$= |Vo| \, 4\pi X'' \frac{R}{\omega L}.$$

By detecting and amplifying this voltage difference $\Delta V$ by means of the amplifier 9, the nuclear magnetic resonance signal of the desired atomic nuclei can be extracted. This resonance signal is fed to the recorder 10 simultaneously with the signal showing the position of the body P, so that the level of the resonance signal corresponding to each position is recorded in the recorder 10. If the signal level is displayed in the display unit 11, the distribution of the specific atomic nuclei in each position of the body P can be obtained.

The foregoing description has been directed to the case, in which continuous high-frequency waves are generated from the oscillator 6 so that the distribution of the specific atomic nuclei in each position of the body P may be measured. In order to measure the relaxation time of the specific atomic nuclei in the body, the resonance intensity at a resonance point is measured while varying the intensity $H_1$ of the vibrating magnetic field emitted from the coil 7 toward the object P. The values of the resonance intensity measured have a tendency to first increase with the increase in the intensity $H_1$ of the vibrating magnetic field and to then decrease, as shown in FIG. 8. The condition for the maximum intensity is given by the following equation:

$$T_1 = 1/(\gamma^2 H_1^2 T_2) \tag{8}$$

In this equation: $T_1$ denotes a spin-lattice relaxation time; and $T_2$ denotes a spin-spin relaxation time. The spin-lattice relaxation time $T_1$ can be calculated from the intensity $H_1$ of the vibrating magnetic field upon the maximum resonance intensity instantly in the case of $T_1 \simeq T_2$ (i.e., in the case of a liquid). In another case, the spin-lattice relaxation time $T_1$ can be calculated from the intensity $H_1$ of the vibrating magnetic field upon the maximum resonance intensity if the spin-spin relaxation time $T_2$ is known.

If, on the other hand, the Helmholtz coil shown in FIGS. 9(a) and (b) is used as a magnet for generating the gradient magnetic field, the magnetic field generated on the axis joining the centers of two coils $CL_1$ and $CL_2$ is in parallel with that axis and has an intensity given by the following equation:

$$H(z) \simeq \frac{3I}{4a}\left(1 - \frac{2Z}{a}\right) \tag{9}$$

so that a magnetic field which is gradient in the axial direction (i.e., in the direction Z) can be generated. In this equation, "a" denotes the radius of the coils $CL_1$ and $CL_2$ and the distance in between; I denotes the current to flow in the opposite directions through the two coils $CL_1$ and $CL_2$; and Z denotes the distance from the coil $CL_1$.

As the magnets for generating the static magnetic field, incidentally, either permanent magnets or electromagnetic magnets including super-conductive magnets, can be employed.

As a method of scanning with the beam-shaped static magnetic field, the body P may be scanned with the frequency of the electromagnetic waves (or the vibrating magnetic field) as applied through the coil 7. In addition, if the intensity of the static magnetic field is changed, the overall intensity is shifted, while the magnetic field is kept gradient, so that the resonance point on the beam-shaped magnetic field is shifted, thereby to make it possible to effect the scanning operations. However, since the static magnetic field is required to have a high stability, it is not advisable to change the intensity of the static magnetic field. It is therefore desirable to arrange a small variable static magnetic field in parallel with a large static magnetic field so that the intensity of the static magnetic field may be affected.

Thus, the distribution and relaxation time of a specific atomic nucleus at any position in a body to be examined can be measured, so that the biochemical information concerning the inside of the body (especially information concerning malignant tissue or the like) can be obtained without any surgical operation.

Incidentally, this invention should not be limited only to the embodiment thus far described with reference to the accompanying drawings but can be variously modified and practiced within such a range as is free from changing the inventive concept thereof.

For example, pulsating high-frequency waves may be generated in place of steady (or continuous) high-frequency waves from the oscillator 6 so that they irradiate the body P through the coil 7. If, at this time, the width tp of the pulses is defined by the following equation (giving so-called "90 degree pulses").

$$\gamma H_1 tp = \pi/2,$$

the signal, i.e., the so-called "free induction decay" (FID) signal, which is induced in the coil 7 after the irradiation with the pulses, will decay with the time constant defined by the relaxation time $T_2$. The signal, which results from subjecting the FID signal to the Fourier transformation, is known to give a resonance signal in the frequency of the aforementioned high-frequency waves.

If the 90 degree pulses are applied, while the gradient magnetic field is being applied, so that the FID signal is amplified by the amplifier 9 and simultaneously subjected to the Fourier transformation, both the distribution of the specific atomic nucleus at each position of the beam-shaped magnetic field and the mean relaxation time $T_2$ can be attained without any scanning with the high-frequency waves and the magnetic field. These processes will be explained in more detail with reference to FIGS. 1(a) to (d).

The pulses (or the 90 degree pulses) for turning the magnetization M along an axis Z' 90 degrees to an axis Y' in a rotating frame, as shown in FIG. 10(a), are applied. After that, the magnetization M decays at the time constant $T_2$, while rotating in the coordinate X-Y plane as shown in the static frame in FIG. 10(b). As a result, there is established in the coil 7 the signal, i.e., the FID signal, which is to be excited by the motions of that magnetization M, as shown in FIG. 10(c). If the decay due to the time constant $T_2$ is subtracted from that of the FID signal and then the Fourier transformation is performed, the concentration distribution of the specific atomic nucleus for the resonance frequency $\omega$ is attained, as shown in FIG. 10(d).

Since the difference in the resonance frequency $\omega$ is made to correspond to the displacement of the position in the direction Z by the gradient magnetic field, the concentration distribution of the atomic nucleus and its relaxation time $T_2$ are instantly attained. If the latter pulses and the FID signal are taken for different positions of the body P, the concentration distribution of the specific atomic nucleus and its relaxation time $T_2$ are attained for the transverse section of the body P.

The measurement of the relaxation time $T_1$ can be obtained by the so-called 180° pulse-t-90° method. First, 180° pulses are applied to turn the magnetization M in the direction of $-Z'$, as shown in FIG. 11(a). After the relaxation for the time t, the 90° pulses are applied, as shown in FIG. 11(b), so that the initial value Mz (t) of the FID signal shown in FIG. 11(c) is obtained. If that value is plotted against the time t, the relationship expressed by the following equation is obtained, as shown in FIG. 11(d):

$$Mz(t) = Mo\left(1 - 2\exp\left(\frac{-t}{T_1}\right)\right). \tag{10}$$

from which the relaxation time $T_1$ can be deduced.

On the other hand, if the NMR signal is taken at different positions of the shims for focusing the static magnetic field into a beam shape on the object P along a transverse section, similar results to those in case the body is moved can be attained.

What is claimed is:

1. A nuclear magnetic resonance apparatus for registering the nuclear magnetic resonance condition of atomic nuclei distributed in a body, the apparatus comprising:

first magnetic field generating means for generating a homogeneous static magnetic field said generating means including magnetic means for focusing the homogeneous static magnetic field into a thin beam shape for application to a selected portion of the body, said magnetic focusing means including a pair of electromagnets and a D.C. stabilized power supply for driving a pair of electromagnets;

second magnetic field generating means for simultaneously generating a gradient magnetic field of smaller intensity than that of the beam-shaped static magnetic field and of such distribution as to gradually increase or decrease in the direction of said beam-shaped static magnetic field;

an oscillator for generating electromagnetic waves having a frequency corresponding to the nuclear magnetic resonance condition of the atomic nuclei to be measured;

a coil wound around the body to be examined, at least a portion of said coil lying in said magnetic fields, impressing said electromagnetic waves upon said body and detecting the nuclear magnetic resonance in said body;

drive means for moving said body in a direction perpendicular to the beam-shaped magnetic field;

a receiver for receiving and processing the nuclear magnetic resonance signal detected by said coil;

a recorder for recording the nuclear magnetic resonance signal processed by said receiver in synchronism with the operation of said drive means for identifying the recorded resonance signal with the position of said body; and a display unit for reading the records as to a desired region of the body out of said recorder and for selectively or simultaneously displaying the distribution and relaxation time of the relevant atomic nuclei in said body.

2. The nuclear magnetic resonance apparatus of claim 1 wherein said electromagnets are superconductive electromagnets.

3. The nuclear magnetic resonance apparatus of claim 1 wherein said magnetic field focusing means includes shims made of a magnetic substance.

4. The nuclear magnetic resonance apparatus of claim 3 wherein said shims are magnetically mounted on said magnet means and slidably movable thereon.

5. The nuclear magnetic resonance apparatus of claim 1 wherein said second magnetic field generating means includes D.C. electromagnets.

6. A method for determining the distribution of specific atomic nuclei in a body comprising the steps of:

applying the magnetic field of stationary magnetic means to a homogeneous static magnetic field for focusing the static magnetic field into a thin beam shape for application through a selected portion of the body;

superimposing on the static magnetic field a gradient magnetic field of smaller intensity than the static magnetic field and of such distribution as to gradually increase or decrease in the direction of the beam-shaped magnetic field; and impressing electromagnetic waves on the body in a planar configuration within said thin beam shape for identifying the nuclear magnetic resonance of the atomic nuclei, the source of said electromagnetic waves being at a known distance from said body.

7. The method of claim 6 also including the step of progressively varying the frequency of the electromagnetic waves for identifying the nuclear magnetic resonance of the atomic nuclei along said thin beam magnetic field.

8. The method of claim 6 wherein the frequency of the electromagnetic waves is held constant and wherein the impressing step includes varying at least one of the intensity and the distribution of the gradient magnetic field for identifying the nuclear magnetic resonance of the atomic nuclei along said thin beam magnetic field.

9. The method of claim 6 wherein the impressing step includes the step of applying pulsating oscillations of a high frequency on the body for identifying the distribution and measuring the relaxation time of the atomic nuclei along the magnetic field of thin beam shape.

* * * * *